US010281954B1

(12) United States Patent
Zhao

(10) Patent No.: US 10,281,954 B1
(45) Date of Patent: May 7, 2019

(54) WEARABLE ELECTRONIC DEVICE

(71) Applicant: Mobvoi Information Technology Co., LTD., Beijing (CN)

(72) Inventor: Zhide Zhao, Beijing (CN)

(73) Assignee: Mobvoi Information Technology Co., LTD, Beijing (CN)

( * ) Notice: Subject to any disclaimer, the term of this patent is extended or adjusted under 35 U.S.C. 154(b) by 0 days.

(21) Appl. No.: 15/989,118

(22) Filed: May 24, 2018

(30) Foreign Application Priority Data

Mar. 20, 2018 (CN) .......................... 2018 1 0230745
May 22, 2018 (WO) ................ PCT/CN2018/087905

(51) Int. Cl.
| | |
|---|---|
| *H04W 4/18* | (2009.01) |
| *G06F 1/16* | (2006.01) |
| *A61B 5/00* | (2006.01) |
| *G06F 3/0488* | (2013.01) |
| *G06F 3/0354* | (2013.01) |
| *G06F 3/041* | (2006.01) |
| *G04G 21/08* | (2010.01) |

(52) U.S. Cl.
CPC .............. *G06F 1/163* (2013.01); *A61B 5/681* (2013.01); *G04G 21/08* (2013.01); *G06F 3/03547* (2013.01); *G06F 3/041* (2013.01); *G06F 3/04883* (2013.01)

(58) Field of Classification Search
CPC ............ G06F 21/35; G06F 1/163; H04B 5/00
USPC ........ 455/556.1, 458, 575.6, 557, 573, 41.1, 455/41.2, 411, 413, 414.1; 342/357.31, 342/357.71, 367
See application file for complete search history.

(56) References Cited

U.S. PATENT DOCUMENTS

| | | | | |
|---|---|---|---|---|
| 4,673,936 | A * | 6/1987 | Kotoh ....................... | G01S 1/68 342/385 |
| 2010/0112964 | A1* | 5/2010 | Yi ........................ | G04G 9/0064 455/90.3 |
| 2015/0182130 | A1* | 7/2015 | Utter, II ............... | A61B 5/0205 600/483 |

(Continued)

*Primary Examiner* — Congvan Tran
(74) *Attorney, Agent, or Firm* — HDC IP Law, LLP

(57) ABSTRACT

An embodiment of the present invention relates to a wearable electronic device, relates to the field of wearable devices, and mainly aims to solve the technical problem of relatively poor wireless communication quality of a smart swatch. The following major technical scheme is adopted: a wearable electronic device comprises a wearing-side shell, a communication-side shell opposite to the wearing-side shell, and a circuit chip board. An accommodation space is formed between the wearing-side shell and the communication-side shell. A metal region of the communication-side shell serves as a metal antenna, and the metal antenna has a feeder terminal and a ground terminal. The circuit chip board is disposed in the accommodation space and comprises a communication module, an antenna feed pin electrically connected to the communication module, and an antenna ground pin electrically connected to the communication module, wherein the antenna feed pin is electrically connected to the feeder terminal of the metal antenna, and the antenna ground pin is electrically connected to the ground terminal of the metal antenna. The wearing-side shell is a metal shell. The wearable electronic device has relatively high wireless communication capability in use.

8 Claims, 4 Drawing Sheets

(56) References Cited

U.S. PATENT DOCUMENTS

2016/0287152 A1* 10/2016 Schwartz ............ A61B 5/14546
2018/0228370 A1* 8/2018 Wang ................... A61B 5/0205

* cited by examiner

US 10,281,954 B1

WEARABLE ELECTRONIC DEVICE

CROSS REFERENCE TO RELATED APPLICATIONS

This application is based upon and claims the benefit of priority of Chinese patent application No. 201810230745.5 filed on Mar. 20, 2018, the contents of which are incorporated herein by reference in its entirety.

TECHNICAL FIELD

An embodiment of the present invention relates to the field of wearable devices, and more particularly relates to a wearable electronic device.

BACKGROUND ART

Wearable devices, for example, smart watches may have more advantages than a traditional mechanical watch and thus gain the popularity among users.

Compared with a mechanical watch, a smart watch may typically have the function of Internet access. For example, a mart watch may allow query of weather forecast and achieve the communication function of a mobile phone. In the realization of the Internet access communication function, a smart watch is required to be provided with an antenna having the communication function. According to the approach actually in use, the antenna is nested into a plastic shell of the smart watch. Thus, when a user wears the smart watch, the electromagnetic waves emitted by the antenna of the smart watch may be heavily dissipated by the wrist of the user, resulting in poor performance of the antenna during the use of the smart watch. As a result, the wireless communication quality of the smart watch is reduced.

SUMMARY OF THE INVENTION

In view of this, an embodiment of the present invention provides a wearable electronic device, and mainly aims to solve the technical problem of relatively poor wireless communication quality of a smart swatch.

To achieve the above objectives, the present invention mainly provides the following technical schemes.

In one aspect, an embodiment of the present invention provides a wearable electronic device, comprising: a wearing-side shell; a communication-side shell opposite to the wearing-side shell, wherein an accommodation space is formed between the wearing-side shell and the communication-side shell; a metal region of the communication-side shell serves as a metal antenna, and the metal antenna has a feeder terminal and a ground terminal; and a circuit chip board disposed in the accommodation space and comprising a communication module, an antenna feed pin electrically connected to the communication module, and an antenna ground pin electrically connected to the communication module, wherein the antenna feed pin is electrically connected to the feeder terminal of the metal antenna, and the antenna ground pin is electrically connected to the ground terminal of the metal antenna; and the wearing-side shell is a metal shell.

The objectives of the present invention and the solution of the technical problems thereof can also be implemented by using the following technical measures.

Optionally, the above wearable electronic device further comprises: a display screen and/or touch screen, wherein a screen placement space is provided on the inner side of the communication-side shell, and the display screen and/or touch screen is disposed in the screen placement space.

Optionally, in the above wearable electronic device, the antenna ground pin is electrically connected to the wearing-side shell.

Optionally, in the above wearable electronic device, a first metal elastic piece and a second metal elastic piece are disposed on a first side surface of the circuit chip board; the first metal elastic piece is electrically connected with the antenna feed pin, and the second metal elastic piece is electrically connected with the antenna ground pin; the first metal elastic piece elastically props against a first electric connection terminal of the metal antenna so that the antenna feed pin is electrically connected with the feeder terminal of the metal antenna; and the second metal elastic piece elastically props against a second electric connection terminal of the metal antenna so that the antenna ground pin is electrically connected with the ground terminal of the metal antenna.

Optionally, in the above wearable electronic device, a third metal elastic piece is disposed on a second side surface of the circuit chip board; the third metal elastic piece is electrically connected with the antenna ground pin; and the third metal elastic piece elastically props against a ground terminal of the wearing-side shell so that the antenna ground pin is electrically connected with the wearing-side shell.

Optionally, in the above wearable electronic device, the metal antenna is in a loop form and surrounds the periphery of the display screen and/or touch screen.

Optionally, in the above wearable electronic device, the metal antenna and the display screen and/or touch screen are separated by a spacing distance; or the metal antenna is attached on an outer wall of the touch screen.

Optionally, in the above wearable electronic device, an outline dimension of the wearing-side shell is greater than an outline dimension of the metal antenna; and when the wearable electronic device is worn on a corresponding body part of a wearer, a projection of the metal antenna in a direction of the body part fully falls into the wearing-side shell.

Optionally, the above wearable electronic device further comprises: an insulating shell disposed between the wearing-side shell and the communication-side shell.

The communication-side shell is an all-metal shell.

Optionally, the above wearable electronic device is a smart electronic watch, a smart electronic bracelet, a smart electronic waistband, or a smart electronic necklace.

By means of the above technical schemes, the wearable electronic device provided by the technical schemes have at least the following advantages:

In the technical schemes provided by the embodiments of the present invention, the wearable electronic device can be worn on the corresponding body part of a wearer with the wearing-side shell of the wearable electronic device facing this body part and the communication-side back on to this body part. The communication module may emit a wireless communication signal outward by means of the metal antenna of the communication-side shell. The wearing-side shell, which is made of a metal, can reflect the wireless communication signal emitted outward by the metal antenna and can reduce the influence of the body part on the wireless communication signal emitted outward by the metal antenna. Therefore, compared with the prior art, the wearable electronic device has high communication capability.

The above descriptions are general descriptions of the technical schemes of the present invention. To provide a clearer understanding of the technical means of the present invention and implement them according to the disclosure of the description, detailed descriptions are made below with preferred embodiments of the present invention in conjunction with the accompanying drawings.

BRIEF DESCRIPTION OF THE DRAWINGS

Numerous additional advantages and benefits will become apparent to those of ordinary skill in the art upon reading the following detailed descriptions of the preferred embodiments. The drawings are merely used to illustrate the objectives of preferred embodiments and cannot be construed as limitations to the present invention. In the whole drawings, like reference numerals represent like components. In the drawings.

DETAILED DESCRIPTION OF THE INVENTION

To further explain the technical means adopted to achieve the intended objectives of the invention and effects thereof, specific implementation modes, structures and features of a wearable electronic device provided according to the present invention and effects thereof will be described in detail below in conjunction with the drawings and preferred embodiments. In the following descriptions, "an embodiment" or "embodiment" in different positions may not necessarily refer to the same embodiment. In addition, specific features, structures or characteristics in one or more embodiments may be combined in any suitable form.

Figure 1:
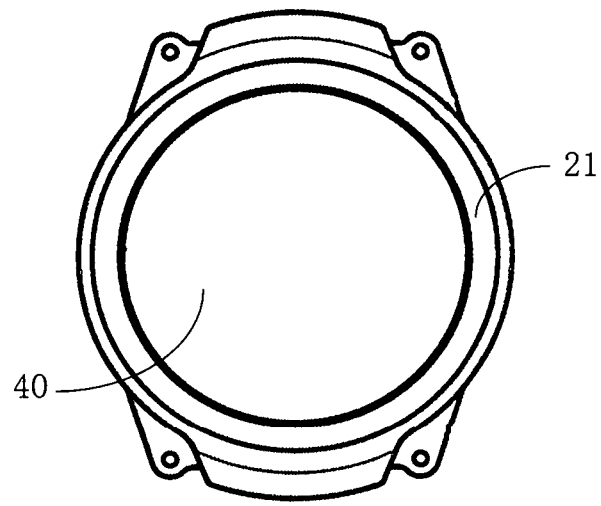
FIG. 1 is a schematic structural diagram of a wearable electronic device provided by an embodiment of the present invention.
Figure 2:
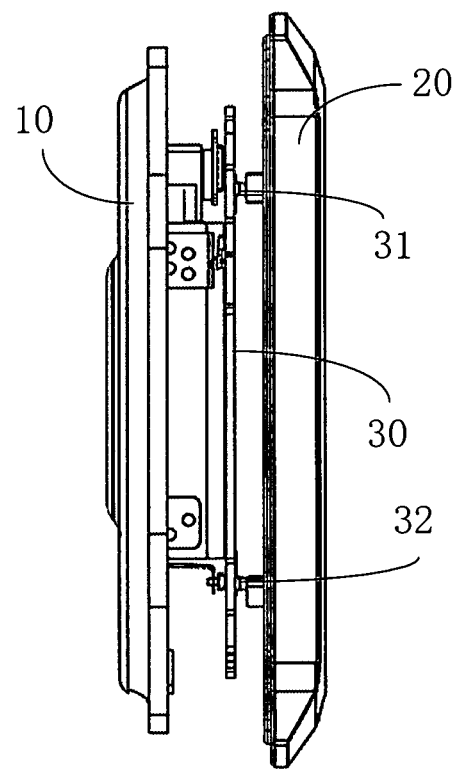
FIG. 2 is a schematic internal structure diagram of a wearable electronic device provided by an embodiment of the present invention.

FIG. 1 and FIG. 2 illustrate an embodiment of a wearable electronic device provided in the present invention. With reference to FIG. 1 and FIG. 2, the wearable electronic device provided in the present invention may be a smart electronic watch, a smart electronic bracelet, a smart electronic waistband, a smart electronic necklace, or the like, and can be worn on the corresponding body parts of a wear. The wearable electronic device includes: a wearing-side shell 10 (rear shell), a communication-side shell 20 (front shell), and a circuit chip board 30. The communication-side shell 20 is opposite to the wearing-side shell 10, and an accommodation space is formed between the wearing-side shell 10 and the communication-side shell 20. A metal region of the communication-side shell 20 serves as a metal antenna 21. The metal antenna 21 has a feeder terminal and a ground terminal. The circuit chip board 30 is arranged in the accommodation space. The circuit chip board 30 includes a communication module, an antenna feed pin 31 electrically connected to the communication module, and an antenna ground pin 32 electrically connected to the communication module. The antenna feed pin 31 is electrically connected with the feeder terminal of the metal antenna 21, and the antenna ground pin 32 is electrically connected with the ground terminal of the metal antenna 21. The wearing-side shell 10 is a metal shell.

The wearable electronic device may be worn on the corresponding body part of the wear with the wearing-side shell of the wearable electronic device facing this body part and the communication-side back on to this body part. The communication module may emit a wireless communication signal outward by means of the metal antenna of the communication-side shell. The wearing-side shell, which is made of a metal, can reflect the wireless communication signal emitted outward by the metal antenna and can reduce the influence of the body part on the wireless communication signal emitted outward by the metal antenna. Therefore, compared with the prior art, the wearable electronic device has high communication capability.

The wearing-side shell may be interpreted as a rear shell facing the side of a wearer's body part when the wearable electronic device can be worn on this body part. The wearing-side shell may be an integrated structure integrally formed by a metal material. The communication-side shell may be interpreted as a front shell back on to a wearer's body part when the wearable electronic device can be worn on this body part. The wearable electronic device also comprises an insulating shell. The insulating shell is disposed between the wearing-side shell and the communication-side shell so that the wearing-side shell and the communication-side shell can be positioned oppositely to form the accommodation space therebetween. The communication-side shell may be an all-metal shell.

In specific implementation, an outer edge of the communication-side shell is fastened with a first side outer edge of the insulating shell, and an outer edge of the wearing-side shell is fastened with a second side outer edge of the insulating shell. Alternately, the communication-side shell comprises an insulating shell. The metal antenna is disposed on the inner side of the insulating shell. The inside of the insulating shell inclines to the central region of the insulating shell. The outer edge of the insulating shell is opposite to the outer edge of the wearing-side shell, and the insulating shell and the wearing-side shell can be directly fastened with each other so that the wearing-side shell and the communication-side shell can be positioned oppositely. The antenna feed pin is electrically connected to the feeder terminal of the metal antenna, where the electric connection is direct electric connection or indirect electric connection. The ground pin of the antenna is electrically connected to the ground terminal of the metal antenna, where the electric connection is direct electric connection or indirect electric connection.

The outline dimension of the wearing-side shell is greater than the outline dimension of the metal antenna. When the wearable electronic device is worn on the corresponding body part of the wearer, the projection of the metal antenna in the direction of the body part fully falls into the wearing-side shell. The metallic wearing-side shell can achieve a good signal enhancement effect.

The communication module is not limited to one. For example, a mobile communication module, a Bluetooth communication module, and a WIFI communication module may be included. Correspondingly, the metal antenna is also not limited to one, and a plurality of signal antennas may serve as signal antennas of different communication modules, respectively.

Figure 3:
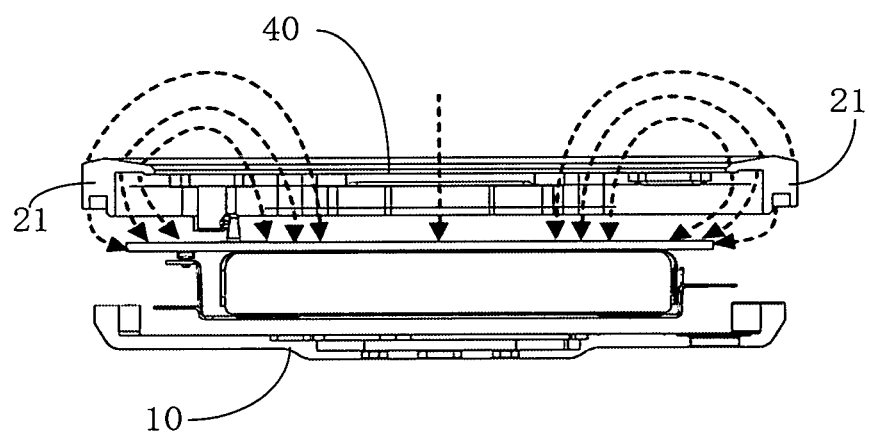
FIG. 3 is a schematic electric field diagram of a wearable electronic device provided by an embodiment of the present invention.

Most wearable electronic devices have a display function, and/or have a touch function. As shown in FIG. 1 and FIG. 3, the wearable electronic device comprises a display screen and/or a touch screen 40. There is a screen placement space on the inner side (central region) of the communication-side shell, and the display screen and/or touch screen 40 can be disposed in the screen placement space.

A relative dielectric constant εr of the display screen and/or touch screen 40 is approximately equal to 6. Under the condition that the antenna ground pin is not electrically connected to the wearing-side shell, part of radiation of the metal antenna 21 passes through the display screen and/or touch screen 40. The wearing-side shell 10 plays a scattering effect on the electromagnetic waves emitted by the metal antenna 21.

Figure 4:
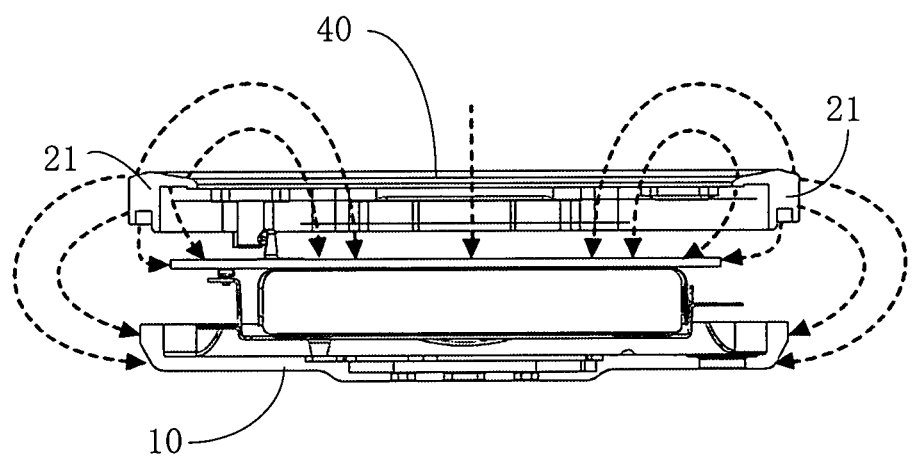
FIG. 4 is a schematic electric field diagram of another wearable electronic device provided by an embodiment of the present invention.

In other embodiments of the present invention, as shown in FIG. 4, the antenna ground pin is electrically connected to the wearing-side shell 20. The electric connection between the antenna ground pin and the wearing-side shell may specifically include direct electric connection or indirect electric connection. Compared with the embodiment that the antenna ground pin is not electrically connected with the wearing-side shell, part of the electromagnetic waves emitted by the metal antenna may radiate toward the outside of the metal antenna 21 (i.e., outside the display screen and/or touch screen) rather than in the previous direction of passing through the display screen and/or touch screen 40. Thus, the intensity of the electric field passing through a high loss dielectric such as the display screen and/or touch screen 40 is reduced. According to the dielectric loss density formula $\omega = \sigma \times E^2$, it can be seen that when the electric field intensity E in a dielectric is reduced, the resulting dielectric loss is reduced. According to the law of conservation of energy, the energy radiating in space increases, resulting in good communication performance of the metal antenna.

In some assembly embodiments, the circuit chip board comprises a first side surface and a second side surface opposite to the first side surface. The circuit board chip board may be fixed to the wearing-side shell first, and then the antenna ground pin is electrically connected to the wearing-side shell. A first metal elastic piece and a second metal elastic piece are disposed on the first side surface of the circuit chip board. The first metal elastic piece is electrically connected with the antenna feed pin, and the second metal elastic piece is electrically connected with the antenna ground pin. The wearing-side shell and the communication-side shell are positioned oppositely. The first metal elastic piece elastically props against a first electric connection terminal of the metal antenna so that the antenna feed pin is electrically connected with the feeder terminal of the metal antenna. The second metal elastic piece elastically props against a second electric connection terminal of the metal antenna so that the antenna ground pin is electrically connected with the ground terminal of the metal antenna. That is, after the wearing-side shell and the communication-side shell are positioned relatively, the electric connection between the antenna feed pin and the feeder terminal of the metal antenna can be achieved. The antenna ground pin is electrically connected with the ground terminal of the metal antenna to enable operation.

Figure 5:
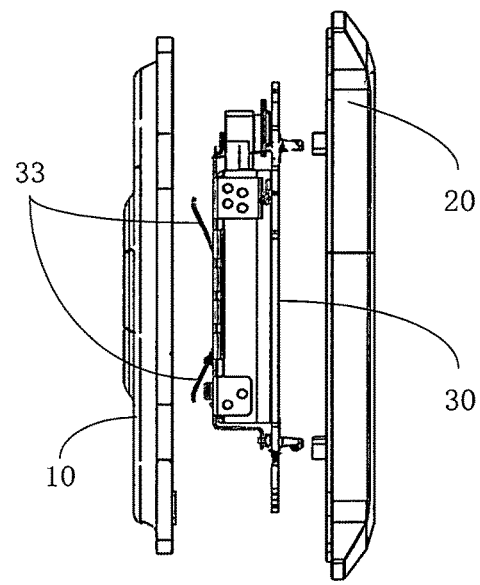
FIG. 5 is an exploded schematic internal structure diagram of a wearable electronic device provided by an embodiment of the present invention.

In other assembly embodiments, as shown in FIG. 5, the circuit chip board comprises a first side surface and a second side surface opposite to the first side surface. The circuit board chip board 30 may be fixed to the communication-side shell 20 first. Then, the antenna feed pin is electrically connected to the feeder terminal of the metal antenna, and the antenna ground pin is electrically connected to the ground terminal of the metal antenna. A third metal elastic piece 33 is disposed on the second side surface of the circuit chip board 30. The third metal elastic piece 33 is electrically connected with the antenna ground pin. The wearing-side shell 10 and the communication-side shell are positioned oppositely. The third metal elastic piece 33 elastically props against a ground terminal of the wearing-side shell 10 so that the antenna ground pin is electrically connected with the wearing-side shell. That is, after the wearing-side shell and the communication-side shell are positioned relatively, the electric connection between the antenna ground pin and the wearing-side shell can be achieved to enable operation. The third metal elastic piece is not limited to one, and two or more than two third metal elastic pieces may used to achieve stable electric connection.

The metal antenna may be in a loop form and surround the periphery of the display screen and/or touch screen. The ring-like metal antenna may be an open-loop or closed-loop antenna. The shape of the loop may match the shape of the display screen and/or touch screen. For example, the display screen and/or touch screen is circular, and the metal antenna may be ring-shaped. The display screen and/or touch screen is rectangular, and the metal antenna may be rectangular ring-shaped.

The metal antenna and the display screen and/or touch screen are separated by a spacing distance. In the prior art, to enable the antenna of a smart watch to meet the operating requirement, a nonmetal material needs to be packed between the antenna surrounding a display panel and the display panel, leading to a relatively low screen-to-body proportion of the smart watch. In an embodiment provided by the present invention, the metal antennal may be attached on the outer wall of the touch screen. Compared with the prior art, the screen-to-body proportion of the wearable electronic device may be increased. As a result, a higher screen-to-body proportion and higher appearance design flexibility of products can be achieved without reducing a user's communication experience in actual use.

Figure 6:
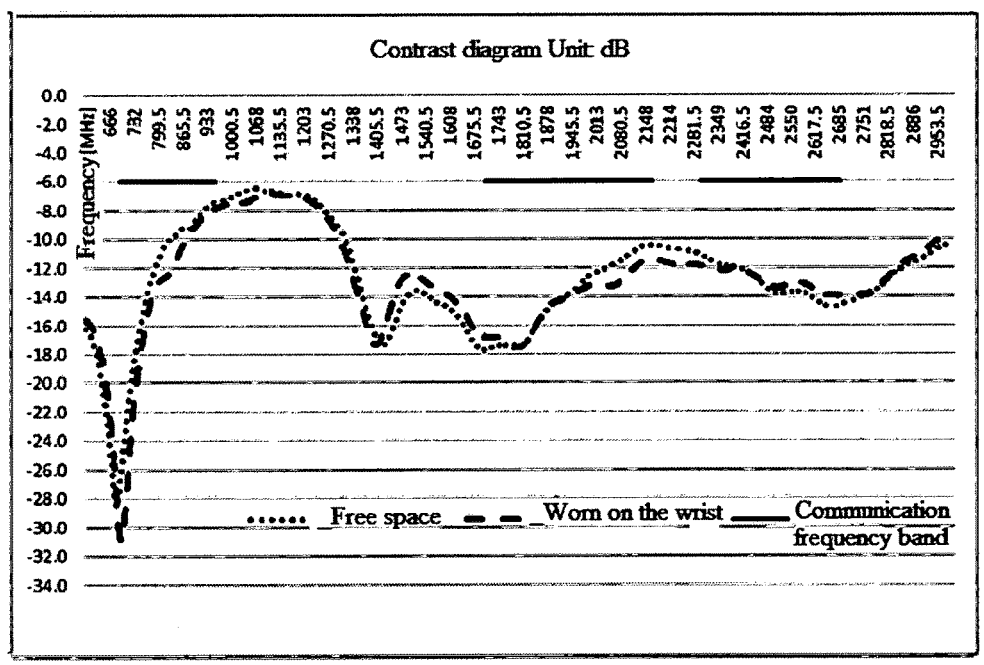
FIG. 6 is a schematic resonance frequency diagram of a wearable electronic device provided by an embodiment of the present invention.
Figure 7:
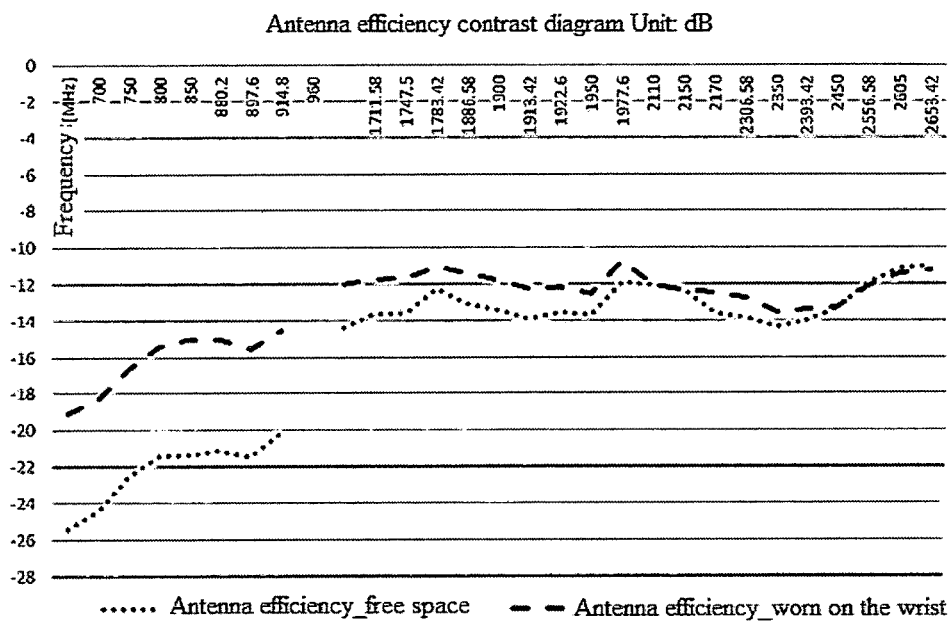
FIG. 7 is a schematic antenna efficiency diagram of a wearable electronic device provided by an embodiment of the present invention.

In the technical schemes provided by the embodiments of the present invention, FIG. 6 illustrates a diagram of antenna resonance test data of the wearable electronic device provided by the embodiments of the present invention that is worn on the wrist and in free space when not worn, and FIG. 7 illustrates a diagram of antenna efficiency test data of the wearable electronic device provided by the embodiments of the present invention that is worn on the wrist and in free space when not worn. In a communication frequency band 700 MHz to 2690 MHz, when a user wears the wearable electronic device and does not wear the wearable electronic device (free space), the antenna has substantially consistent resonance state. In a low frequency band 700 MHz to 960 MHz, the antenna efficiency is improved by about 6 dB when the wearable electronic device is worn in contrast to that when the wearable electronic device is not worn (free space). In a high frequency band 1710 MHz to 2690 MHz, the antenna efficiency can be improved by about 2 dB at most when the wearable electronic device is worn in contrast to that when the wearable electronic device is not worn (free space).

Figure 8:
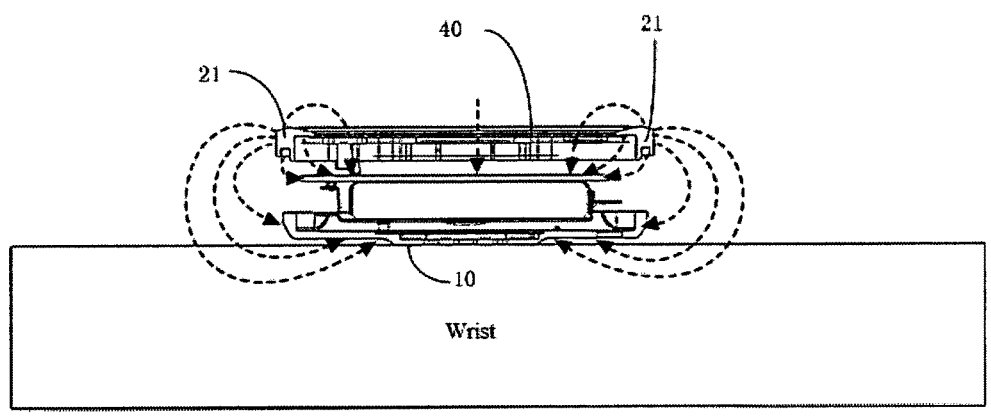
FIG. 8 is a schematic electric field diagram of a wearable electronic device worn on a wrist provided by an embodiment of the present invention.

According to the technical schemes provided by the embodiments of the present invention, as shown in FIG. 8, when the user wears the wearable electronic device, the user's wrist may have strong guiding effect on the electric field radiated by the metal antenna 21 due to its high relative dielectric constant εr that is approximately equal to 26 (compared with the relative dielectric constant εr of the display screen and/or touch screen 40 that is approximately equal to 6) and far greater than the relative dielectric constant of the display screen and/or touch screen 40. Moreover, due to the presence of the metallic wearing-side shell 10 between the metal antenna 21 and the wrist, more electric field radiates toward the outside of the metal antenna (outside the display screen and/or touch screen, not passing through the display screen and/or touch screen). Thus, the electric field passing through the high loss dielectric such as the display screen and/or touch screen 40 is reduced. According to the dielectric loss density formula $\omega=\sigma \times E^2$, it can be seen that the less the electric field E passing through the dielectric is, the lower the dielectric loss is. Accordingly the metal antenna can radiate more energy, resulting in good communication performance of the metal antenna.

In the above embodiments, the descriptions of various embodiments are emphasized differently, and a reference for the part not described in detail in an embodiment can be made to related descriptions of other embodiments.

It can be understood that the relevant features in the above device can be mutually referenced. In addition, the terms "first", "second" and the like in the above embodiments are used for distinguishing various embodiments, and do not represent the advantages and disadvantages of the embodiments.

In the specification provided herein, numerous specific details are described. However, it is to be understood that the embodiments of the present invention can be practiced without these specific details. In some examples, well-known structures and techniques are not shown in detail in order not to obscure the understanding of the specification.

Similarly, it should be understood that various features of the present invention sometimes are grouped into a single embodiment, drawing or description thereof in the above descriptions of the exemplary embodiments of the present invention for the sake of simplifying the disclosure and helping understanding one or more of various invention aspects. However, the disclosed device should not be interpreted as reflecting the following intention: the claimed invention requires more features than those expressly recited in each claim. Rather, as reflected by following claims, the invention aspects are less than all features of a single embodiment disclosed above. Accordingly, a claim following a specific embodiment is hereby expressly incorporated into this embodiment, wherein each claim serves as an individual embodiment of the present invention.

Those skilled in the art can understand that the components of the device in an embodiment can be adaptively modified and arranged in one or more devices different from the embodiment. The components in an embodiment may be combined into one component, and in addition, they may be divided into a plurality of sub-components. Except that at least some of such features are mutually exclusive, all of the features disclosed in the present description (including accompanying claims, abstract and drawings) and all components of any device disclosed so can be combined in any combination. Unless explicitly stated otherwise, each feature disclosed in the present description (including accompanying claims, abstract, and drawings) can be replaced by an alternative feature that provides the same, equivalent, or similar purpose.

In addition, those skilled in the art can understand that although some embodiments described herein include some features included in other embodiments rather than other features, combinations of features of different embodiments are meant to be within the scope of the present invention and form different embodiments. For example, in the following claims, any one of the claimed embodiments can be used in any combination manner. Various component embodiments of the present invention may be implemented by hardware, or in a combination thereof.

It should be noted that the above embodiments are intended to illustrate the present disclosure rather than to limit the present invention, and alternative embodiments can be devised by those skilled in the art without departing from the scope of the appended claims. In the claims, any reference symbols between brackets should not be constructed as limitations to the claims. The term "comprising" does not preclude the presence of a component or assembly that is not listed in the claims. The terms "a" or "an" before a component or assembly do not preclude the presence of a plurality of such components or assemblies. The present invention can be implemented by means of a device comprising a plurality of different components. In a claim in which a plurality of components are listed, the plurality of such components can be embodied by the same component item. The use of the terms "first", "second", "third" and the like does not represent any order. Such terms can be interpreted as names.

The above are merely descriptions of the preferred embodiments of the present invention, and not intended to limit the present invention in any form. Any simple changes, equivalent alterations and modifications made to the above embodiments according to the technical essence of the present invention should still fall within the scope of the technical schemes of the present invention.

I claim:

1. A wearable electronic device, comprising:
   a wearing-side shell;
   a communication-side shell opposite to the wearing-side shell, wherein an accommodation space is formed between the wearing-side shell and the communication-side shell; a metal region of the communication-side shell serves as a metal antenna, and the metal antenna has a feeder terminal and a ground terminal; and
   a circuit chip board disposed in the accommodation space and comprising a communication module, an antenna feed pin electrically connected to the communication module, and an antenna ground pin electrically connected to the communication module,
   wherein the antenna feed pin is electrically connected to the feeder terminal of the metal antenna, and the antenna ground pin is electrically connected to the ground terminal of the metal antenna; and the wearing-side shell is a metal shell,
   the antenna ground pin is electrically connected to the wearing-side shell, and
   the communication-side shell comprises an insulating shell, the metal antenna is at an inner side of the insulating shell, the insulating shell is directly fastened with the wearing-side shell so that the wearing-side shell and the communication-side shell are positioned oppositely.

2. The wearable electronic device according to claim 1, further comprising:
a display screen and/or touch screen,
wherein a screen placement space is provided on the inner side of the communication-side shell, and the display screen and/or touch screen is disposed in the screen placement space.

3. The wearable electronic device according to claim 1, wherein
a first metal elastic piece and a second metal elastic piece are disposed on a first side surface of the circuit chip board; the first metal elastic piece is electrically connected with the antenna feed pin, and the second metal elastic piece is electrically connected with the antenna ground pin;
the first metal elastic piece elastically props against a first electric connection terminal of the metal antenna so that the antenna feed pin is electrically connected with the feeder terminal of the metal antenna; and
the second metal elastic piece elastically props against a second electric connection terminal of the metal antenna so that the antenna ground pin is electrically connected with the ground terminal of the metal antenna.

4. The wearable electronic device according to claim 1, wherein
a third metal elastic piece is disposed on a second side surface of the circuit chip board; the third metal elastic piece is electrically connected with the antenna ground pin; and the third metal elastic piece elastically props against a ground terminal of the wearing-side shell so that the antenna ground pin is electrically connected with the wearing-side shell.

5. The wearable electronic device according to claim 1, wherein
the metal antenna is in a loop form and surrounds an periphery of the display screen and/or touch screen.

6. The wearable electronic device according to claim 5, wherein
the metal antenna and the display screen and/or touch screen are separated by a spacing distance; or
the metal antenna is attached on an outer wall of the display screen and/or touch screen.

7. The wearable electronic device according to claim 1, wherein
an outline dimension of the wearing-side shell is greater than an outline dimension of the metal antenna; and
when the wearable electronic device is worn on a corresponding body part of a wearer, a projection of the metal antenna in a direction of the corresponding body part fully falls into the wearing-side shell.

8. The wearable electronic device according to claim 1, wherein
the wearable electronic device is a smart electronic watch, a smart electronic bracelet, a smart electronic waistband, or a smart electronic necklace.

* * * * *